United States Patent
Rho et al.

(10) Patent No.: US 10,251,862 B2
(45) Date of Patent: Apr. 9, 2019

(54) COSMETIC COMPOSITION CONTAINING HYDROXY PYRANONE DERIVATIVE COMPOUND FOR PROMOTING DIFFERENTIATION OF ADIPOCYTES

(71) Applicant: AMOREPACIFIC CORPORATION, Seoul (KR)

(72) Inventors: Ho Sik Rho, Yongin-si (KR); Heung Soo Baek, Yongin-si (KR); Yu Jung Kim, Yongin-si (KR); Song Seok Shin, Yongin-si (KR); John Hwan Lee, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

(21) Appl. No.: 15/107,955

(22) PCT Filed: Jan. 20, 2015

(86) PCT No.: PCT/KR2015/000560
§ 371 (c)(1),
(2) Date: Jun. 24, 2016

(87) PCT Pub. No.: WO2015/108394
PCT Pub. Date: Jul. 23, 2015

(65) Prior Publication Data
US 2016/0324824 A1 Nov. 10, 2016

(30) Foreign Application Priority Data
Jan. 20, 2014 (KR) .................. 10-2014-0006640

(51) Int. Cl.
*A61K 31/357* (2006.01)
*A61K 31/36* (2006.01)
(Continued)

(52) U.S. Cl.
CPC ............ *A61K 31/357* (2013.01); *A61K 8/498* (2013.01); *A61K 31/36* (2013.01); *A61Q 19/00* (2013.01);
(Continued)

(58) Field of Classification Search
CPC ...... A61K 31/357; A61K 8/498; A61K 31/36; A61K 2800/92; A61K 2800/91; A61K 2800/74; A61Q 19/08; A61Q 19/00
See application file for complete search history.

(56) References Cited

U.S. PATENT DOCUMENTS 6,916,844 B2 7/2005 Roh et al.
8,586,540 B2 11/2013 You et al.
(Continued)

FOREIGN PATENT DOCUMENTS

CN 1662526 8/2005
CN 101945884 1/2011
(Continued)

OTHER PUBLICATIONS

Wollina et al (Clinical Interventions in Aging 2017:12 2069-2076) (Year: 2017).*
(Continued)

*Primary Examiner* — Angela C Brown-Pettigrew
(74) *Attorney, Agent, or Firm* — Cantor Colburn LLP

(57) ABSTRACT

The present invention relates to a cosmetic composition containing a hydroxypyranone derivative compound as an active ingredient for promoting the differentiation of adipocytes. The composition according to the present invention has an effect of promoting the differentiation of adipocytes, and thus allows the differentiation of adipocyte in a skin layer, thereby increasing the skin volume or elasticity. Therefore, the composition of the present invention can be
(Continued)

ADSC control   IDX control

IDX + Example 1 (30 μM)   IDX + 30 μM glibenclamide
(maximum effect)

variously used as a cosmetic composition or a pharmaceutical composition in the field, such as skin damage.

5 Claims, 1 Drawing Sheet

(51) Int. Cl.
*A61K 8/49* (2006.01)
*A61Q 19/00* (2006.01)
*A61Q 19/08* (2006.01)

(52) U.S. Cl.
CPC .......... *A61Q 19/08* (2013.01); *A61K 2800/74* (2013.01); *A61K 2800/91* (2013.01); *A61K 2800/92* (2013.01)

(56) References Cited

U.S. PATENT DOCUMENTS

| | | | |
|---|---|---|---|
| 8,853,174 B2 | 10/2014 | Kameyama et al. | |
| 2003/0236299 A1* | 12/2003 | Roh | A61K 8/498 514/452 |
| 2010/0331272 A1* | 12/2010 | Kameyama | A61K 8/63 514/33 |
| 2012/0107427 A1 | 5/2012 | Kim et al. | |
| 2012/0141399 A1 | 6/2012 | You et al. | |

FOREIGN PATENT DOCUMENTS

| | | |
|---|---|---|
| EP | 2551342 | 1/2013 |
| KR | 100482668 | 4/2005 |
| KR | 1020090130801 | 12/2009 |
| KR | 1020110106235 | 9/2011 |
| KR | 101078419 | 10/2011 |
| KR | 101206097 | 11/2012 |
| KR | 1020130107865 | 10/2013 |

OTHER PUBLICATIONS

Lindolfo da Silva Meirelles, et al., "Mesenchymal stem cells reside in virtually all post-natal organs and tissues", Journal of Cell Science, vol. 119, No. 11, (2006), pp. 2204-2213.

Mark F. Pittenger, et al., "Multilineage Potential of Adult Human Mesenchymal Stem Cells", Science, Vlol. 284, (Apr. 2, 1999), pp. 143-148.

Y. Xu, et al., "The use of small interfering RNAs to inhibit adipocyte differentiation in human preadipocytes and fetal-femur-derived mesenchymal cells", Experimental Cell Research, vol. 312, (2006), pp. 1856-1864.

International Search Report—PCT/KR2015/000560 dated Mar. 27, 2015.

Written Opinion—PCT/KR2015/000560 dated Mar. 27, 2015.

Ho Sik Rho, et al., "Kojyl cinnamate ester derivatives promote adiponectin production during adipogenesis in human adipose tissue-derived mesenchymal stem cells", Bioorganic & Medicinal Chemistry letters, vol. 24, (2014), pp. 2141-2145.

Kim, et al., "The effects of a novel synthetic retinoid, seletinoid G, on the expression of extracellular matrix proteins in aged human skin in vivo", Chinica Chimica Acta, vol. 362, (2005), pp. 161-169.

Extended European Search Report—European Application No. 15737765.6 dated May 30, 2017.

Chinese Office Action—Chinese Patent Application No. 201580003446.2 dated May 15, 2018.

* cited by examiner

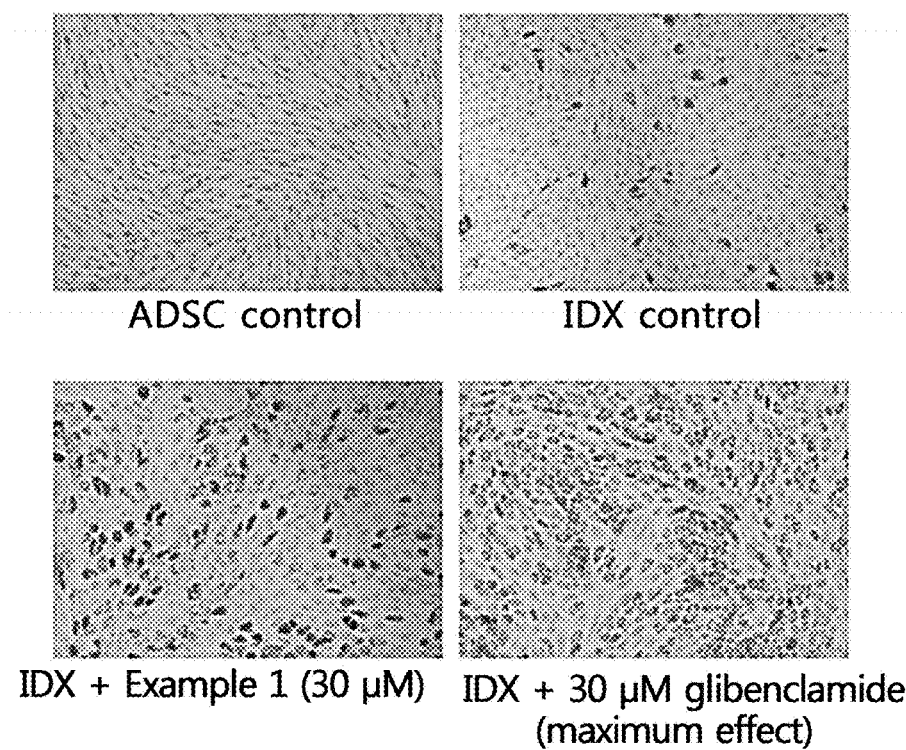

COSMETIC COMPOSITION CONTAINING HYDROXY PYRANONE DERIVATIVE COMPOUND FOR PROMOTING DIFFERENTIATION OF ADIPOCYTES

TECHNICAL FIELD

The present disclosure relates to a cosmetic composition for promoting differentiation of adipocytes.

BACKGROUND ART

The basic structure of skin is maintained by subcutaneous adipose tissue. The subcutaneous adipose tissue plays a critical role in maintaining skin's volume and strength. Accordingly, increasing the volume of adipose tissue can be a better solution for maintaining skin's volume and elasticity than the existing methods of providing elasticity to the outer dermal or epidermal layer. Various researches are being actively conducted on adipocytes. In general, preadipocytes are widely used because they are differentiated into adipocytes by differentiation-inducing substances such as insulin. Recently, mesenchymal stem cells are gaining focus in researches using adipocytes. The adipose-derived mesenchymal stem cells are widely used in studying the differentiation of adipocytes (*Science* 1999, 284, 143-146) because they can be differentiated in a manner similar to the differentiation of preadipocytes into adipocytes (*Exp. Cell Res.* 2006, 312, 1856-1864). The adipose-derived mesenchymal stem cells are widely distributed throughout the body and are known to be capable of being differentiated not only to adipocytes but also other types of cells such as cartilage cells, bone cells, etc. (*J. Cell Sci.* 2006, 119, 2204-2213).

DISCLOSURE

Technical Problem

The inventors of the present disclosure have studied on compounds exhibiting the effect of promoting differentiation of adipocytes. In doing so, they have found out that a hydroxypyranone derivative having a particular structure exhibits the effect of promoting differentiation of adipocytes and have completed the present disclosure.

Accordingly, the present disclosure is directed to providing a composition for promoting differentiation of adipocytes or enhancing skin volume or elasticity, which contains the hydroxypyranone derivative compound.

Technical Solution

In an aspect, the present disclosure provides a composition for promoting differentiation of adipocytes or enhancing skin volume or elasticity, which contains a hydroxypyranone derivative as an active ingredient.

Advantageous Effects

A composition according to the present disclosure, which contains a hydroxypyranone derivative as an active ingredient, exhibits an effect of promoting differentiation of adipocytes and, through this, exhibits an effect of enhancing skin volume or elasticity. More specifically, it may exhibit the effect of enhancing skin volume and elasticity by promoting differentiation of human mesenchymal stem cells into adipocytes and thereby producing lipid droplets. Accordingly, the composition of the present disclosure may be variously applied in cosmetic or pharmaceutical field.

BRIEF DESCRIPTION OF DRAWINGS

FIG. 1 shows microscopic images showing the result of inducing differentiation of adipocytes using a hydroxypyranone derivative compound according to an aspect of the present disclosure.

BEST MODE

Korean Patent Application No. 10-2014-0006640 filed on Jan. 20, 2014 is incorporated in its entirety into the present disclosure for all purposes. The present disclosure also claims priority to Korean Patent Application No. 10-2014-0006640 the content of which is incorporated in its entirety into the present disclosure.

In an aspect, the present disclosure may relate to a composition for enhancing skin volume or elasticity, which contains a hydroxypyranone derivative compound represented by Chemical Formula 1 as an active ingredient:

[Chemical Formula 1]

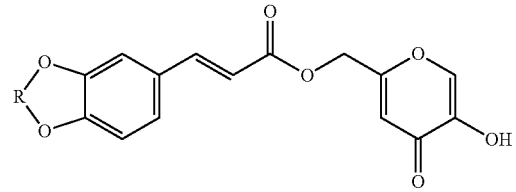

wherein R is —$CH_2$— or —$CH_2CH_2$—.

In an aspect, the present disclosure may relate to a method for enhancing skin volume or elasticity, which includes administering the hydroxypyranone derivative compound represented by Chemical Formula 1 or a composition containing the same as an active ingredient to a subject in need of enhancement of skin volume or elasticity. In an aspect of the present disclosure, the administration may be performed according to an administration method and an administration dosage described in the present disclosure.

In an aspect, the present disclosure may relate to the hydroxypyranone derivative compound represented by Chemical Formula 1 or a composition containing the same as an active ingredient for use in enhancement of skin volume or elasticity.

In an aspect, the present disclosure may relate to a use of the hydroxypyranone derivative compound represented by Chemical Formula 1 for enhancement of skin volume or elasticity. In an aspect, the present disclosure may relate to a use of the hydroxypyranone derivative compound represented by Chemical Formula 1 in preparation of a composition for enhancing skin volume or elasticity.

In an aspect of the present disclosure, the composition according to an aspect of the present disclosure may promote differentiation of mesenchymal stem cells into adipocytes.

In an aspect of the present disclosure, the mesenchymal stem cells may be human mesenchymal stem cells.

In an aspect of the present disclosure, the composition according to an aspect of the present disclosure may contain the active ingredient at a concentration of 0.01-100 μM based on the total volume of the composition. In an aspect of the present disclosure, the concentration of the active ingredient may be 0.001 µM or higher, 0.01 µM or higher, 0.1 µM or higher, 0.5 µM or higher, 1 µM or higher, 5 µM or higher, 10 µM or higher, 20 µM or higher, 25 µM or higher, 28 µM or higher, 29 µM or higher, 30 µM or higher, 31 µM or higher, 32 µM or higher, 35 µM or higher, 40 µM or higher, 50 µM or higher, 100 µM or higher, 200 µM or higher, 500 µM or higher, 1 mM or higher, 10 mM or higher, 50 mM or higher, 100 mM or higher, 1 M or higher or 5 M or higher and 10 M or lower based on the total volume of the composition. Specifically, in an aspect of the present disclosure, the concentration of the active ingredient may be 30 µM.

In an aspect of the present disclosure, the composition according to an aspect of the present disclosure may increase adipose tissue.

In an aspect of the present disclosure, the composition according to an aspect of the present disclosure may increase skin volume.

In an aspect of the present disclosure, the composition according to an aspect of the present disclosure may increase skin elasticity.

In an aspect of the present disclosure, the composition according to an aspect of the present disclosure may be a pharmaceutical, food or cosmetic composition.

In an aspect, the present disclosure may relate to a method for preparing the hydroxypyranone derivative represented by Chemical Formula 1, which includes:

(1) a step of preparing 5-hydroxy-2-(chloromethyl)-4H-pyran-4-one by replacing the hydroxyl group of the hydroxymethyl group at 2-position of 5-hydroxy-2-(hydroxymethyl)-4H-pyran-4-one;

(2) preparing a metal salt by reacting 3,4-(methylenedioxy)cinnamic acid or 3,4-(ethylenedioxy)cinnamic acid with an inorganic base in a polar solvent; and (3) reacting the 5-hydroxy-2-(chloromethyl)-4H-pyran-4-one with the metal salt.

The preparation method is described with Scheme 1 as an example.

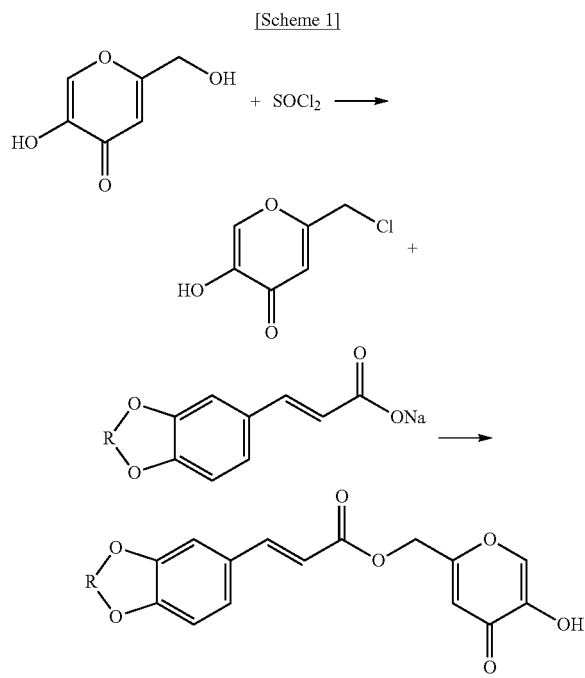

wherein R is —$CH_2$— or —$CH_2CH_2$—.

Specific examples of the hydroxypyranone derivative compound of Chemical Formula 1 obtained by the preparation method according to an aspect of the present disclosure include (2E)-(5-hydroxy-4-oxo-4H-pyran-2-yl)methyl 3-(benzo[d][1,3]dioxo-6-yl)acrylate and (2E)-(5-hydroxy-4-oxo-4H-pyran-2-yl)methyl 3-(2,3-dihydroxybenzo[b][1,4]dioxo-7-yl)acrylate.

In an aspect, the present disclosure may relate to a composition for enhancing skin volume or elasticity, which contains a hydroxypyranone derivative compound prepared by the preparation method according to an aspect of the present disclosure as an active ingredient.

Because the hydroxypyranone derivative compound represented by Chemical Formula 1 prepared by the preparation method according to an aspect of the present disclosure is capable of producing and accumulating lipid droplets by promoting differentiation of adipocytes, it can improve skin elasticity and enhance skin volume.

In an aspect, the present disclosure may relate to a composition for promoting differentiation of adipocytes, which contains the hydroxypyranone derivative compound represented by Chemical Formula 1 as an active ingredient.

[Chemical Formula 1]

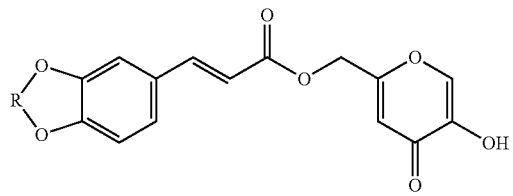

wherein R is —$CH_2$— or —$CH_2CH_2$—.

In an aspect, the present disclosure may relate to a method for promoting differentiation of adipocytes, which includes administering the hydroxypyranone derivative compound represented by Chemical Formula 1 or a composition containing the same as an active ingredient to a subject in need of promotion of adipocyte differentiation. In an aspect of the present disclosure, the administration may be performed according to an administration method and an administration dosage described in the present disclosure.

In an aspect, the present disclosure may relate to the hydroxypyranone derivative compound represented by Chemical Formula 1 or a composition containing the same as an active ingredient for use in promotion of adipocyte differentiation.

In an aspect, the present disclosure may relate to a use of the hydroxypyranone derivative compound represented by Chemical Formula 1 for promotion of adipocyte differentiation. In an aspect, the present disclosure may relate to a use of the hydroxypyranone derivative compound represented by Chemical Formula 1 in preparation of a composition for promoting differentiation of adipocytes.

In the present disclosure, "skin" refers to an organ covering the outer part of an organism, which is composed of the epidermis, the dermis and the subcutaneous fat layer. The term is used in the broadest concept, including not only the tissue that covers the outer part of the face or body but also the scalp and hair.

In the present disclosure, "volume" refers to the volume or capacity of the skin layer. It may mean the apparent voluminous look. Accordingly, skin with increased or enhanced volume will look lifted, healthy and young. And, for example, when skin has been damaged by injury, wound, burn, etc. and has scars or depressions as a result thereof or the skin or tissue has been incised for surgery, etc., enhancement of the volume of skin tissue may lead to increased volume of the damaged tissue and skin layer and provide an effect of restoring the skin or tissue close to its original state.

In the present disclosure, "enhancement of volume" means increased volume of the skin layer. It may also mean lifted and healthy looking skin or restoration of damaged skin tissue close to its original state due to increased skin volume. Accordingly, increased skin tissue volume may provide an effect whereby damaged skin is restored close to its original state as the volume of the drooping skin is increased and the skin surface is stretched.

A formulation of the cosmetic composition according to an aspect of the present disclosure is not specially limited and may be selected adequately depending on purposes. For example, it may be prepared into one or more formulation selected from a group consisting of a skin lotion, a skin softener, a skin toner, an astringent lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

When the cosmetic composition according to an aspect of the present disclosure is formulated as a paste, a cream or a gel, animal fiber, plant fiber, wax, paraffin, starch, tragacanth, a cellulose derivative, polyethylene glycol, silicone, bentonite, silica, talc, zinc oxide, etc. may be used as a carrier ingredient.

When the cosmetic composition according to an aspect of the present disclosure is formulated as a powder or a spray, lactose, talc, silica, aluminum hydroxide, calcium silicate or polyamide powder may be used as a carrier ingredient. In particular, a spray may further contain a propellant such as chlorofluorohydrocarbon, propane/butane or dimethyl ether.

When the cosmetic composition according to an aspect of the present disclosure is formulated as a solution or an emulsion, a solvent, a solubilizer or an emulsifier may be used as a carrier ingredient. For example, water, ethanol, isopropanol, ethyl carbonate, ethyl acetate, benzyl alcohol, benzyl benzoate, propylene glycol, 1,3-butylene glycol, an aliphatic glycerol ester, polyethylene glycol or a fatty acid ester of sorbitan may be used.

When the cosmetic composition according to an aspect of the present disclosure is formulated as a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the cosmetic composition according to an aspect of the present disclosure is formulated as a surfactant-containing cleanser, an aliphatic alcohol sulfate, aliphatic alcohol ether sulfate, sulfosuccinic acid monoester, isethionate, an imidazolinium derivative, methyl taurate, sarcosinate, a fatty acid amide ether sulfate, an alkylamidobetaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

The cosmetic composition according to an aspect of the present disclosure may further contain, in addition to the hydroxypyranone derivative compound, functional additives and other ingredients commonly contained in cosmetic compositions. The functional additive may be an ingredient selected from a group consisting of a water-soluble vitamin, an oil-soluble vitamin, a polypeptide, a polysaccharide, a sphingolipid and a seaweed extract.

If necessary, the cosmetic composition according to an aspect of the present disclosure may contain, in addition to the functional additive, an ingredient commonly contained in cosmetic compositions. The additionally contained ingredient may be an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a fragrance, a blood circulation stimulant, a cooling agent, an antiperspirant, purified water, etc.

In an aspect, the present disclosure may relate to a formulation for external application to skin, which contains the hydroxypyranone derivative compound as an active ingredient. The formulation for external application to skin includes any formulation that can be applied to skin from outside and cosmetics in various formulations may be included therein.

The pharmaceutical composition according to an aspect of the present disclosure may be provided as various oral or parenteral formulations. Usually, the formulation is prepared using a commonly used diluent or excipient such as a filler, an extender, a binder, a humectant, a disintegrant, a surfactant, etc. Solid formulations for oral administration include a tablet, a pill, a powder, a granule and a soft or hard capsule. These solid formulations are prepared by mixing the compound with at least one excipient, e.g., starch, calcium carbonate, sucrose, lactose, gelatin, etc. In addition to the simple excipient, a lubricant such as magnesium stearate, talc, etc. is also used. Liquid formulations for oral administration include a suspension, a solution for internal use, an emulsion, a syrup. In addition to a commonly used simple diluent such as water and liquid paraffin, the formulation may contain various excipients such as a humectant, a sweetener, an aromatic, a preservative, etc. Formulations for parenteral administration include a sterilized aqueous solution, a nonaqueous solution, a suspension, an emulsion, a lyophilized formulation and a suppository. The nonaqueous solution and the suspension may contain propylene glycol, polyethylene glycol, a vegetable oil such as olive oil, an injectable ester such as ethyl oleate, etc. As a base of the suppository, witepsol, macrogol, Tween 61, cocoa butter, laurin butter, glycerogelatin, etc. may be used.

The composition according to an aspect of the present disclosure may contain a pharmaceutically acceptable salt of the compound and may also contain another pharmaceutically active compound. The salt is not particularly limited as long as it is pharmaceutically acceptable. For example, hydrochloride, sulfate, nitrate, phosphate, hydrofluoride, hydrobromide, formate, acetate, tartrate, lactate, citrate, fumarate, maleate, succinate, methanesulfonate, benzenesulfonate, toluenesulfonate, naphthalenesulfonate, etc. may be used.

The composition according to an aspect of the present disclosure may be administered parenterally or orally depending on purposes. A daily dosage of 0.1-500 mg, specifically 1-100 mg, per kg body weight may be administered once or several times a day. The administration dosage for a particular patient may vary depending on the body weight, age, sex and physical condition of the patient, diet, administration time, administration method, excretion rate, severity of disease, etc.

The pharmaceutical composition according to an aspect of the present disclosure may be prepared into any pharmaceutically appropriate formulation including an formulation such as a pill, a granule, a tablet, a soft or hard capsule, a suspension, an emulsion, a syrup, an aerosol, a formulation for external application to skin such as an ointment, a cream, etc., a suppository, an injection, a sterilized solution for injection, etc. Specifically, it may be prepared into an injection or a formulation for external application to skin.

The composition according to an aspect of the present disclosure may be administered to a mammal such as rat, mouse, cattle, human, etc. via various routes. All modes of administration can be expected. For example, it may be administered orally, rectally, intravenously, intramuscularly, subcutaneously, intrauterinarily or intracerebroventricularly.

The composition according to an aspect of the present disclosure may be administered through various routes that can be selected easily by those of ordinary skill in the art. In particular, the pharmaceutical composition according to an aspect of the present disclosure may be administered through the skin surface as a formulation for external application to skin.

In an aspect of the present disclosure, the food composition may be a health functional food composition.

The formulation of the food composition according to an aspect of the present disclosure is not particularly limited. For example, it may be formulated as a tablet, a granule, a powder, a liquid such as a drink, a caramel, a gel, a bar, etc. Each formulation of the food composition may contain, in addition to the active ingredient, an ingredient commonly used in the related art that may be selected by those skilled in the art without difficulty depending on the particular formulation or purpose of use. In this case, a synergic effect may be achieved.

Determination of the administration dosage of the active ingredient in the food composition according to an aspect of the present disclosure is within the level of those skilled in the art. A daily administration dosage may be, for example, 0.1-5000 mg/kg/day, more specifically 50-500 mg/kg/day, although not being limited thereto. The administration dosage may vary depending on various factors such as the age and health condition of a subject, presence or complication(s), etc.

For example, the food composition according to an aspect of the present disclosure may be in the form of various foods such as chewing gum, caramel, candies, frozen dessert, confectionery, etc., drinks such as carbonated beverage, mineral water, alcoholic beverage, etc. or health functional foods including vitamin, mineral, etc.

In addition, the food composition according to an aspect of the present disclosure may contain various nutrients, vitamins, minerals (electrolytes), flavors such as synthetic and natural flavors, colorants, extenders (cheese, chocolate, etc.), pectic acid and its salts, alginic acid and its salts, organic acids, protective colloidal thickeners, pH control agents, stabilizers, antiseptic, glycerin, alcohols, carbonating agents used in carbonated beverages, etc. In addition, the functional food composition according to an aspect of the present disclosure may contain pulp used to prepare natural fruit juice, fruit juice drinks and vegetable drinks. These ingredients may be used either independently or in combination. These additives are usually contained in an amount of about 0-20 parts by weight based on 100 parts by weight of the composition according to an aspect of the present disclosure, although it is of no significant importance.

Hereinafter, the present disclosure will be described in detail through examples and test examples. However, the following examples and test examples are for illustrative purposes only and the present disclosure is not limited by them.

[Example 1] Preparation of (2E)-(5-hydroxy-4-oxo-4H-pyran-2-yl)methyl 3-(benzo[d][1,3]dioxo-6-yl)acrylate 50 g of 5-hydroxy-2-(hydroxymethyl)-4H-pyran-4-one (0.35 mmol) was dissolved in 250 mL of N,N-dimethylformamide. After cooling to 10° C. in an ice-water bath, 50 g of thionyl chloride (0.42 mol) was added dropwise for 30 minutes. After stirring at room temperature for 2 hours, 2000 mL of iced water was added to the reaction solution. The produced solid was filtered and the resulting solid was dissolved in 1000 mL of ethyl acetate. After drying and decoloring using magnesium carbonate and activated carbon and then filtering, a crystal was obtained by concentrating the filtrate and adding hexane. After vacuum filtration, 39.5 g of 5-hydroxy-2-(chloromethyl)-4H-pyran-4-one (70%) was obtained as a yellow solid.

5 g of 3,4-(methylenedioxy)cinnamic acid (0.026 mol) and 1.3 g of sodium hydroxide (0.031 mol) were dissolved in 40 mL of methanol. After distilling the methanol, the remaining residue was dissolved in 70 mL of N,N-dimethylformamide. After adding 4.2 g of 5-hydroxy-2-(chloromethyl)-4H-pyran-4-one (0.026 mol) thereto, the mixture was heated in an oil bath at 110° C. for 2 hours under stirring. After distilling the solvent, the residue was dissolved in 300 mL of ethyl acetate. The ethyl acetate solution was washed with 5% hydrochloric acid and distilled water and then dried and discolored by adding magnesium carbonate and activated carbon. After filtering off the insoluble substance, the filtrate was evaporated under reduced pressure (12 torr) to obtain 5.3 g of the reaction product (65% yield) as a pale yellow solid.

TLC (ethyl acetate:hexane=1:1): $R_f$=0.63.
$^1$H NMR (DMSO-$d_6$, δ): 9.29 (bs, 1H), 8.12 (s, 1H), 7.65 (d, 1H, J=16.2 Hz), 7.46 (s, 1H), 7.23 (d, 1H, J=8.1 Hz), 6.96 (d, 1H, J=8.1 Hz), 6.60 (d, 1H, J=16.2 Hz), 6.52 (s, 1H), 6.08 (s, 2H), 5.07 (s, 2H).

[Example 2] Preparation of (2E)-(5-hydroxy-4-oxo-4H-pyran-2-yl)methyl 3-(2,3-dihydroxybenzo[b][1,4]dioxo-7-yl)acrylate The target product (5.0 g, 57%) was obtained as a pale yellow solid in the same manner as in Example 1, except that 3,4-(ethylenedioxy)cinnamic acid was used instead of 3,4-(methylenedioxy)cinnamic acid.

TLC (ethyl acetate:hexane=1:1): $R_f$=0.58.
$^1$H NMR (DMSO-$d_6$, δ): 9.26 (bs, 1H), 8.11 (s, 1H), 7.63 (d, 1H, J=16.2 Hz), 7.32 (s, 1H), 7.25 (d, 1H, J=8.1 Hz), 6.90 (d, 1H, J=8.1 Hz), 6.59 (d, 1H, J=16.2 Hz), 6.51 (s, 1H), 5.06 (s, 2H), 4.27 (m, 4H).

[Test Example 1] Inducement of Differentiation of Adipose-Derived Mesenchymal Stem Cells into Adipocytes Human adipose-derived mesenchymal stem cells (hAT-MSCs) were purchased form Lonza, Inc. (Walkersville, Md., USA) and cultured according to the instructions of Lonza, Inc. The adipose-derived mesenchymal stem cells were induced to differentiate into adipocytes according to the instructions of Lonza, Inc. except that troglitazone (TRO) was used instead of indomethacin. Specifically, the mesenchymal stem cells were differentiated into adipocytes by adding to a culture of the mesenchymal stem cells 1 g/mL insulin, 1 M dexamethasone (DEXA), 0.5 mM isobutylmethylxanthine (IBMX) and 2 M TRO. To a test group, the compound of Example 1 was added to the medium at a concentration of 30 µM when inducing the differentiation into adipocytes. A positive control group was treated with 30 µM glibenclamide together with IDX. On day 14 after the adipose-derived mesenchymal stem cells began to differentiate into adipocytes, the cells were washed with 10 mL of phosphate-buffered saline (PBS) and then fixed for 10 minutes using a 10% formalin/PBS solution (0.2 mL/cm$^2$). The fixed cells were washed once with a 60% isopropanol solution (0.5 mL/cm$^2$) and lipid bodies in the adipocytes were stained for 10 minutes with Oil Red O dissolved in 60% isopropanol (0.2 mL/cm$^2$). Then, after staining again with hematoxylin to visualize nuclei, the cells were observed under a microscope. The result is shown in FIG. 1.

From FIG. 1, treatment with the compound of Example 1 resulted in increased differentiation into adipocytes as compared to treatment with IDX only. When compared with the glibenclamide as positive control, the number of the stained cells was slightly less but the differentiation into adipocytes was significantly increased. Accordingly, the hydroxypyranone derivative compound according to an aspect of the present disclosure or a composition containing the same can promote the differentiation of adipocytes and, thus, can provide an effect of enhancing skin volume or elasticity.

[Test Example 2] Measurement of Expression Level of Adiponectin in Human Adipose-Derived Mesenchymal Stem Cells Adiponectin is a representative protein hormone secreted in adipocytes. It is reported that the expression of adiponectin is increased with the differentiation into adipocytes. Accordingly, the amount of adiponectin secreted into a cell culture medium was measured as a marker of promotion of adipocyte differentiation. In order to measure the secreted amount of adiponectin, human adipose-derived mesenchymal stem cells purchased form Lonza, Inc. were gathered on day 14 after they began to differentiate into adipocytes and the amount of adiponectin was quantified using an adiponectin ELISA kit (R&D Systems, Cat. No. DY1065) as follows (Data were normalized to that of the control group). Specifically, after reacting with a capture antibody on a 96-well plate and washing with a washing buffer, the cells were treated with a sample at a concentration of 60 µM and incubated at room temperature for 2 hours. Subsequently, the cells were incubated with a detection antibody, HRP, a substrate solution and a stop solution for the time specified in the protocol, while washing 3 times between each step. After the final incubation, absorbance was measured at 450 nm using a spectrophotometer. The result is shown in Table 1.

TABLE 1

| Substance | Expression level of adiponectin Adiponectin (pg/mL, avg ± S.D.) |
|---|---|
| Untreated | 32 ± 11 |
| IDX | 302 ± 50 |
| IDX + glibenclamide | 1832 ± 110 |
| IDX + kojic acid (60 µM) | 312 ± 103 |
| IDX + Example 1 (60 µM) | 1435 ± 113 |
| IDX + Example 2 (60 µM) | 1300 ± 140 |

The compounds of Example 1 and Example 2 are kojic acid ester compounds. As can be seen from Table 1, although kojic acid did not show an effect of increasing adiponectin expression, the compounds of Example 1 and Example 2 increased the expression of adiponectin. The effect of increasing adiponectin expression of the compounds according to the present disclosure was not significantly different from that of the positive control substance glibenclamide. Accordingly, it was confirmed that the hydroxypyranone derivative compound according to an aspect of the present disclosure or a composition containing the same exhibit a remarkable effect of promoting adipocyte differentiation and, thus, can provide an effect of enhancing skin volume or elasticity.

Hereinafter, the present disclosure will be described in detail through formulation examples. However, the following formulation examples are for illustrative purposes only and the present disclosure is not limited by them.

[Formulation Example 1] Soft Capsule

A soft capsule filling solution was prepared by mixing 8 mg of the hydroxypyranone derivative of Example 1 or 2, 9 mg of vitamin E, 9 mg of vitamin C, 2 mg of palm oil, 8 mg of a hydrogenated vegetable oil, 4 mg of yellow beeswax and 9 mg of lecithin according to a commonly employed method. Separately from this, a soft capsule sheet was prepared from 66 parts by weight of gelatin, 24 parts by weight of glycerin and 10 parts by weight of a sorbitol solution and was filled with the filling solution to prepare a soft capsule containing 400 mg of the composition according to an aspect of the present disclosure.

[Formulation Example 2] Tablet 8 mg of the hydroxypyranone derivative of Example 1 or 2, 9 mg of vitamin E, 9 mg of vitamin C, 200 mg of galactooligosaccharide, 60 mg of lactose and 140 mg of maltose were mixed and granulated using a fluidized-bed dryer. After adding 6 mg of sugar ester, 500 mg of the resulting composition was prepared into a tablet according to a commonly employed method.

[Formulation Example 3] Drink 8 mg of the hydroxypyranone derivative of Example 1 or 2, 9 mg of vitamin E, 9 mg of vitamin C, 10 g of glucose, 0.6 g of citric acid and 25 g of oligosaccharide syrup were mixed and 300 mL of purified water was added. 200 mL of the resulting solution was filled per bottle and sterilized at 130° C. for 4-5 seconds.

[Formulation Example 4] Granule 8 mg of the hydroxypyranone derivative of Example 1 or 2, 9 mg of vitamin E, 9 mg of vitamin C, 250 mg of anhydrous crystalline glucose and 550 mg of starch were mixed and granulated using a fluidized-bed granulator. The prepared granule was filled in a pouch.

[Formulation Example 5] Injection

An injection was prepared by a commonly employed method with the composition described in Table 2.

TABLE 2

| Ingredients | Contents |
| --- | --- |
| Hydroxypyranone derivative of Example 1 or 2 | 10-50 mg |
| Sterilized distilled water for injection | adequate |
| pH control agent | adequate |

[Formulation Example 6] Health Functional Food

A health functional food was prepared by a commonly employed method with the composition described in Table 3.

TABLE 3

| Ingredients | Contents |
| --- | --- |
| Hydroxypyranone derivative of Example 1 or 2 | 20 mg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above compositional ratios of the vitamins and minerals are given only as a specific example relatively suitable for a health functional food and may be varied as desired.

[Formulation Example 7] Health Drink

A health drink was prepared by a commonly employed method with the composition described in Table 4.

TABLE 4

| Ingredients | Contents |
| --- | --- |
| Hydroxypyranone derivative of Example 1 or 2 | 1000 mg |
| Citric acid | 1000 mg |
| Oligosaccharide | 100 g |
| Taurine | 1 g |
| Purified water | balance |

According to a common health drink preparation method, the above ingredients were mixed, heated at 85° C. for about 1 hour under stirring, filtered and then sterilized.

[Formulation Example 8] Softening Lotion (Skin Lotion)

A softening lotion was prepared by a commonly employed method with the composition described in Table 5.

TABLE 5

| Ingredients | Contents (wt %) |
| --- | --- |
| Hydroxypyranone derivative of Example 1 or 2 | 0.2 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Antiseptic, pigment and fragrance | adequate |
| Purified water | balance |

[Formulation Example 9] Nourishing Lotion (Milk Lotion)

A nourishing lotion was prepared by a commonly employed method with the composition described in Table 6.

TABLE 6

| Ingredients | Contents (wt %) |
| --- | --- |
| Hydroxypyranone derivative of Example 1 or 2 | 1.0 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Antiseptic, pigment and fragrance | adequate |
| Purified water | balance |

[Formulation Example 10] Nourishing Cream

A nourishing cream was prepared by a commonly employed method with the composition described in Table 7.

TABLE 7

| Ingredients | Contents (wt %) |
| --- | --- |
| Hydroxypyranone derivative of Example 1 or 2 | 2.0 |
| Glycerin | 3.0 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Antiseptic, pigment and fragrance | adequate |
| Purified water | balance |

[Formulation Example 11] Massage Cream

A massage cream was prepared by a commonly employed method with the composition described in Table 8.

TABLE 8

| Ingredients | Contents (wt %) |
| --- | --- |
| Hydroxypyranone derivative of Example 1 or 2 | 2.0 |
| Glycerin | 8.0 |
| Butylene glycol | 4.0 |
| Liquid paraffin | 45.0 |
| β-Glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Antiseptic, pigment and fragrance | adequate |
| Purified water | balance |

[Formulation Example 12] Pack

A pack was prepared by a commonly employed method with the composition described in Table 9.

TABLE 9

| Ingredients | Contents (wt %) |
| --- | --- |
| Hydroxypyranone derivative of Example 1 or 2 | 0.2 |
| Glycerin | 4.0 |
| Polyvinyl alcohol | 15.0 |
| Hyaluronic acid extract | 5.0 |
| β-Glucan | 7.0 |
| Allantoin | 0.1 |
| Nonyl phenyl ether | 0.4 |
| Polysorbate 60 | 1.2 |
| Ethanol antiseptic | 6.0 |
| Antiseptic, pigment and fragrance | adequate |
| Purified water | balance |

While the exemplary embodiments have been shown and described, it will be understood by those skilled in the art that various changes in form and details may be made thereto without departing from the spirit and scope of this disclosure as defined by the appended claims.

The invention claimed is:

1. A method for increasing volume of a damaged subcutaneous adipose tissue of a subject through promoting differentiation of adipocytes, wherein the method comprises administering an effective amount of a hydroxypyranone derivative compound represented by Chemical Formula 1 to the subject in need of increasing volume of a damaged subcutaneous adipose tissue, wherein the hydroxypyranone derivative compound represented by Chemical Formula 1 increases volume of a damaged subcutaneous adipose of the subject through promotion differentiation of adipocytes:

[Chemical Formula 1]

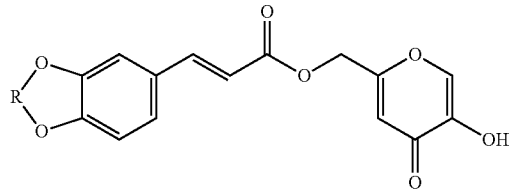

wherein R is —$CH_2$— or —$CH_2CH_2$—.

2. The method according to claim 1, wherein the hydroxypyranone derivative compound promotes differentiation of mesenchymal stem cells into adipocytes.

3. The method according to claim 1, wherein the hydroxypyranone derivative compound is administered in form of a composition, and the composition comprises the hydroxypyranone derivative compound at a concentration of 0.01-100 μM based on the total volume of the composition.

4. The method according to claim 1, wherein the hydroxypyranone derivative compound increases adipose tissue.

5. The method according to claim 3, wherein the composition is a pharmaceutical or cosmetic composition.

* * * * *